US006279376B1

United States Patent
Yamada et al.

(10) Patent No.: US 6,279,376 B1
(45) Date of Patent: Aug. 28, 2001

(54) GAS SENSOR FOR VEHICLE ENGINE HAVING A DOUBLE-PIPE COVER

(75) Inventors: Masaru Yamada, Tokoname; Kengo Toguchi, Takahama; Hidetaka Hayashi, Nagoya; Satoshi Nakamura, Okazaki; Hiroo Imamura, Nukata-gun; Daisuke Makino, Ichinomiya, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/405,837

(22) Filed: Sep. 27, 1999

(30) Foreign Application Priority Data

Sep. 28, 1998 (JP) ................................. 10-272952
Aug. 3, 1999 (JP) ................................. 11-219862

(51) Int. Cl.$^7$ .................. G01N 27/407; G01N 27/58; G01N 27/41
(52) U.S. Cl. .................. 73/23.2; 73/23.32; 73/31.5
(58) Field of Search .................. 73/23.2, 23.31, 73/23.32, 31.05, 866.5; 422/98, 94; 204/428, 409

(56) References Cited

U.S. PATENT DOCUMENTS

| 3,368,386 | * | 2/1968 | Harvey ............................. 73/27 |
| 4,033,170 | * | 7/1977 | Kawamura et al. ................... 73/23 |
| 4,115,235 | * | 9/1978 | Capone ........................... 204/195 S |
| 4,199,424 | * | 4/1980 | Jeitelbaum ....................... 204/195 S |
| 4,222,026 | * | 9/1980 | Heiney, III et al. .................. 338/34 |
| 4,223,293 | * | 9/1980 | Springer et al. .................... 338/34 |
| 4,535,316 | * | 8/1985 | Wertheimer et al. ................. 338/34 |
| 4,756,885 |   | 7/1988 | Raff et al. ......................... 422/98 |
| 4,883,643 | * | 11/1989 | Nishio et al. ..................... 422/94 |
| 5,238,552 |   | 8/1993 | Kato et al. ........................ 204/428 |
| 5,880,353 | * | 3/1999 | Graser et al. ..................... 73/23.2 |
| 5,948,963 | * | 9/1999 | Kato et al. ....................... 73/23.2 |
| 6,164,120 | * | 12/2000 | Friese et al. ..................... 73/23.2 |
| 6,202,469 | * | 3/2001 | Nakamura et al. ................ 73/23.31 |
| 6,214,186 | * | 4/2001 | Watanabe et al. .................. 204/428 |

FOREIGN PATENT DOCUMENTS

| 59-194059 | 12/1984 | (JP) . |
| 2-33167   | 9/1990  | (JP) . |
| 2653831   | 5/1997  | (JP) . |
| 9-222416  | 8/1997  | (JP) . |

* cited by examiner

*Primary Examiner*—Hezron Williams
*Assistant Examiner*—David J. Wiggins
(74) *Attorney, Agent, or Firm*—Pillsbury Winthrop LLP

(57) ABSTRACT

A gas sensor has a housing, a gas sensing element held by the housing and having a gas contact portion and an element cover for covering the gas contact portion. The element cover has a double pipe structure formed by layering an outer pipe and an inner pipe. The outer pipe has an outer bottom portion having an outer bottom hole and an outer side portion having plural outer side holes. The inner pipe has an inner bottom portion having an inner bottom hole and an inner side portion having plural inner side holes disposed not to overlap the outer side holes. A spacing D of 0.2–1.0 mm is formed between the outer bottom portion and the inner bottom portion. As a result, flow resistance in the spacing D is relatively high, and the sample gas sufficiently and more smoothly flows toward the gas sensing element. Therefore, the element cover prevents condensed water from entering the inside of the gas sensor and improves response of the gas sensor.

16 Claims, 17 Drawing Sheets

GAS SENSOR FOR VEHICLE ENGINE HAVING A DOUBLE-PIPE COVER

CROSS REFERENCE TO RELATED APPLICATION

This application relates to and claims priority from Japanese Patent Application Nos. 10-272952 filed on Sep. 28, 1998 and 11-219862 filed on Aug. 3, 1999, the contents of which are hereby incorporated by reference.

BACKGROUND OF THE INVENTION

1. Field of the Invention

The present invention relates to a gas sensor which is suitably used for measuring a concentration of oxygen in exhaust gas, an air-fuel mixture ratio or the like of a vehicle engine.

2. Related Art

Conventionally, in a vehicle engine, a concentration of oxygen in exhaust gas, an air-fuel mixture ratio or the like are detected. Fuel combustion of the engine is controlled according to the detected values so that energy is more saved, exhaust gas is more efficiently purified and so on. As a gas sensor for detecting a concentration of oxygen or the like in exhaust gas (sample gas), a gas sensor having a gas sensing element made of solid electrolyte such as zirconia is known.

There are various kinds of the gas sensing elements including a cup-shaped gas sensing element having one end closed and a rectangular-shaped layered type gas sensing element formed by layering sheet members. Each of the gas sensing element has a gas contact portion to directly contact the sample gas. The gas contact portion is exposed in the sample gas for air-fuel mixture ratio detection. Since the gas sensing element is made of solid electrolyte, the gas sensing element is relatively fragile, and it may be difficult to continuously use the gas sensing element in the sample gas. Therefore, the gas sensing element is generally covered by an element cover for protection. The element cover needs to have an opening through which the sample gas flows toward the gas contact portion. However, depending on a position or a shape of the opening, condensed water contained in the sample gas may directly adhere to the gas sensing element and break the gas sensing element.

To cope with this problem, various gas sensors in which an element cover prevents condensed water from adhering to the gas sensing element while maintaining flow characteristics of the sample gas to the gas contact portion are developed. JP-Y2-2-33167 discloses such a gas sensor having a single-pipe structure element cover for protecting a gas sensing element. JP-U-59-194059 and JP-A-9-222416 also disclose such gas sensors having a double-pipe structure element cover for protecting a gas sensing element. The double-pipe element cover is made of an outer pipe and an inner pipe both having plural openings.

In JP-A-9-222416, as shown in FIG. 23, a gas sensor 9 includes a gas sensing element 10 having a gas contact portion 11, a housing 4 for holding the gas sensing element 10 and an element cover 90 secured to the housing 4 for covering the gas contact portion 11. The element cover 90 has a double pipe structure formed by layering an outer pipe 91 and an inner pipe 92. The outer pipe 91 has a side portion having plural outer side holes 911 and a bottom portion having an outer bottom hole 912. The inner pipe 92 also has a side portion having plural inner side holes 921 and a bottom portion having an inner bottom hole 922. The outer side holes 911 and the inner side holes 921 are disposed not to overlap each other. The element cover 90 is designed to protect the gas sensing element 10, prevent condensed water from adhering to the gas sensing element 10 and improve flow characteristics of the sample gas within the element cover 90 so that response of the gas sensor 9 is improved.

However, although the gas sensing element 10 is sufficiently protected by the element cover 90 and condensed water is prevented from adhering to the gas sensing element 10, flow characteristics of the sample gas within the element cover 90 is not sufficiently improved. That is, a speed of introduction of the sample gas to the gas sensing element 10 is relatively small, thereby worsening response of the gas sensor 9.

SUMMARY OF THE INVENTION

In view of the foregoing problems, it is an object of the present invention to provide a gas sensor having an element cover which protects a gas sensing element, prevents condensed water from entering inside of the gas sensor and improves response of the gas sensor.

According to the present invention, a gas sensor has a gas sensing element having a gas contact portion to contact sample gas, a housing for holding the gas sensing element and an element cover connected to the housing and covering the gas contact portion. The element cover has a double pipe structure formed by layering an inner pipe and an outer pipe. Each of the inner pipe and the outer pipe is formed into a cylindrical shape with a bottom. The inner pipe has a side portion including a first side portion having a side hole through which the sample gas flows and a second side portion which prevents the sample gas from flowing therethrough, and a bottom portion having a bottom hole through which the sample gas flows. The outer pipe also has a side portion having a side hole through which the sample gas flows and a bottom portion having a bottom hole through which the sample gas flows. The second side portion of the inner pipe is exposed through the side hole of the outer pipe, and a spacing of 0.2–1.0 mm is formed between the bottom portion of the inner pipe and the bottom portion of the outer pipe. Therefore, the sample gas introduced into the element cover through the side hole of the outer pipe does not directly contact the gas contact portion, but first contacts the inner pipe and then flows through the side hole of the inner pipe toward the gas contact portion. As a result, condensed water in the sample gas is prevented from directly contacting and damaging the gas sensing element. Further, since the spacing between the bottom portion of the inner pipe and the bottom portion of the outer pipe is as small as 0.2–1.0 mm, flow resistance of the sample gas in the spacing is relatively large. Therefore, the sample gas entering between the outer pipe and inner pipe tends to flow into the inner side hole rather than into the spacing. As a result, the sample gas is sufficiently and more smoothly introduced to the gas contact portion, thereby improving response of the gas sensor.

BRIEF DESCRIPTION OF THE DRAWINGS

This and other objects and features of the present invention will become more readily apparent from a better understanding of the preferred embodiments described below with reference to the accompanying drawings, in which.

DETAILED DESCRIPTION OF THE PREFERRED EMBODIMENTS

Figure 1:
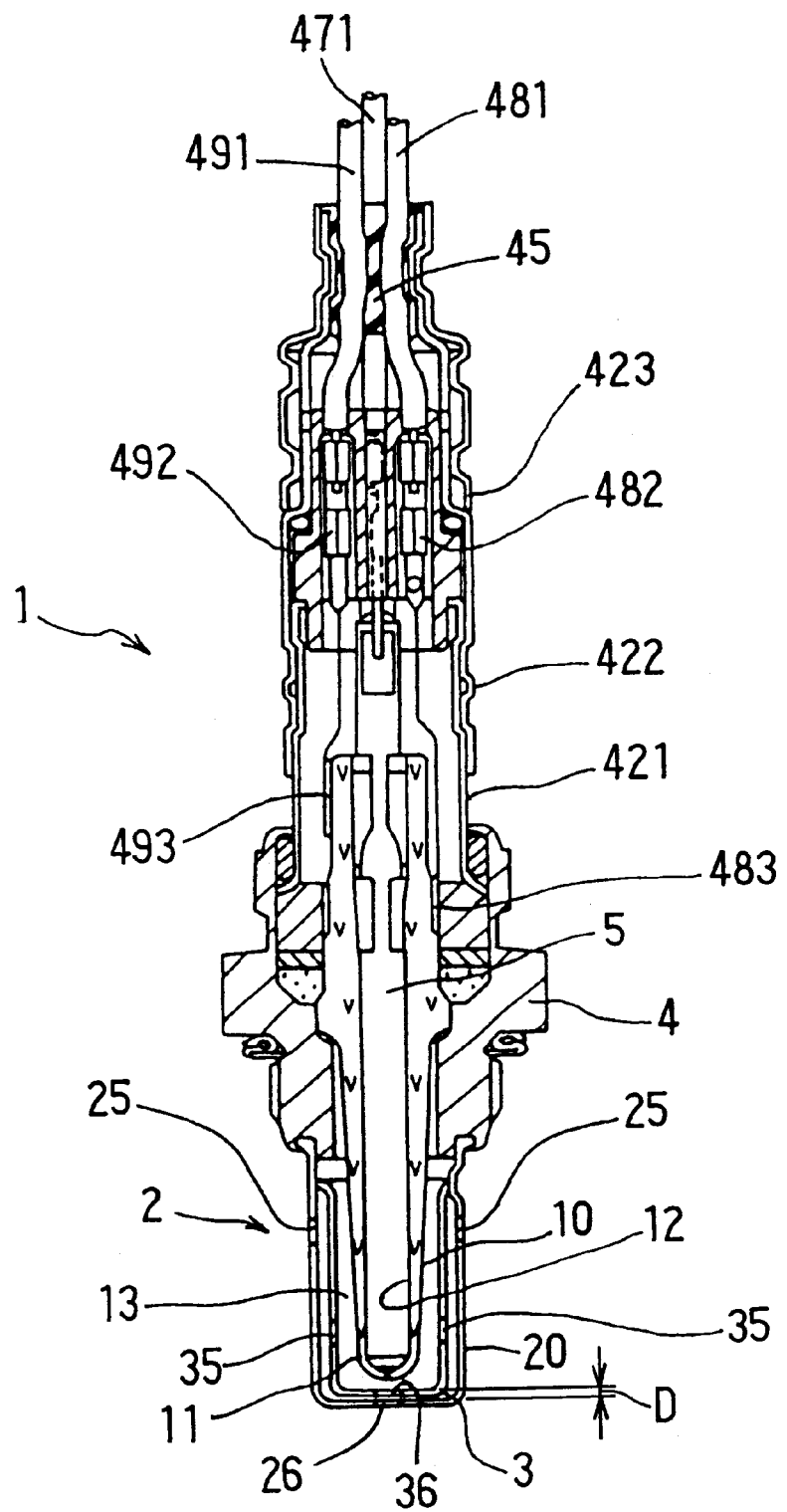
FIG. 1 is a schematic sectional view showing a gas sensor according to a first preferred embodiment of the present invention.

Preferred embodiments of the present invention will be described hereinafter with reference to the accompanying drawings. In the embodiments following a first preferred embodiment of the present invention, components which are substantially the same as those in the first embodiment are assigned the same reference numerals, and the explanation thereof are omitted in the following embodiments.

Figure 2:
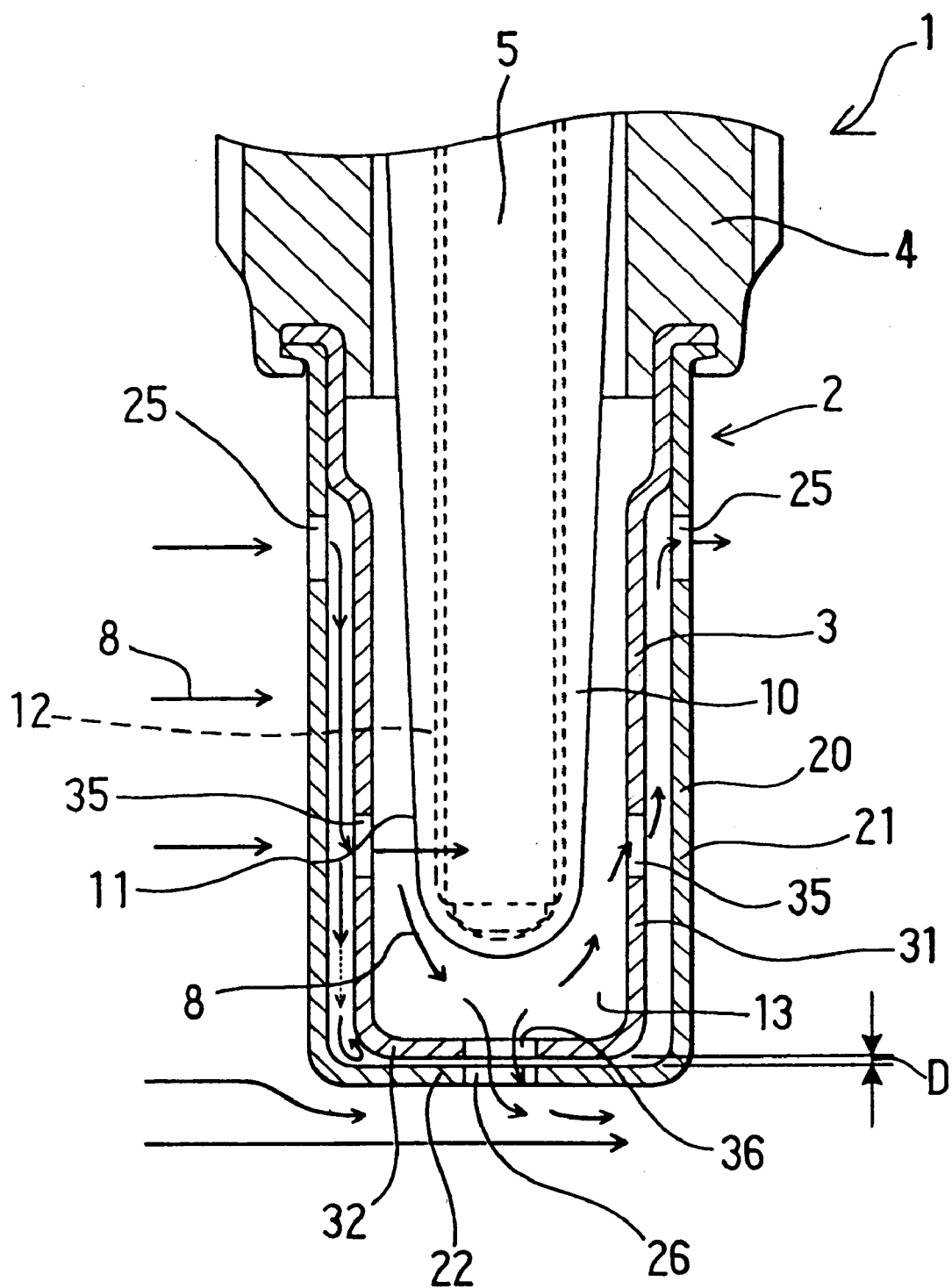
FIG. 2 is a schematic sectional view showing a gas sensing element and an element cover of the gas sensor according to the first embodiment.

The first embodiment is described with reference to FIGS. 1–4. As shown in FIGS. 1 and 2, a gas sensor 1 is an oxygen sensor for a vehicle engine, and has a gas sensing element 10 having a gas contact portion 11 to contact sample gas, a housing 4 for holding the gas sensing element 10 and an element cover 2 secured to the housing 4 for covering the gas contact portion 11. The element cover 2 has a double pipe structure formed by layering an outer pipe 20 and an inner pipe 3. Each of the outer pipe 20 and the inner pipe 3 is formed into a cylindrical shape having a bottom at an lower end in FIG. 1. As shown in FIG. 2, the outer pipe 20 has a side portion 21 (hereinafter referred to as outer side portion 21) having plural holes 25 (hereinafter referred to as outer side holes 25), and a bottom portion 22 (hereinafter referred to as outer bottom portion 22) having a hole 26 (hereinafter referred to as outer bottom hole 26). The inner pipe 3 also has a side portion 31 (hereinafter referred to as inner side portion 31) having plural holes 35 (hereinafter referred to as inner side holes 35), and a bottom portion 32 (hereinafter referred to as inner bottom portion 32) having a hole 36 (hereinafter referred to as inner bottom hole 36). The sample gas flows through each holes 25, 35, 26 and 36. The outer side holes 25 and the inner side holes 35 are disposed not to overlap each other. That is, the gas sensing element 10 can not be seen through the outer side holes 25 from outside. Further, a spacing D of 0.2–1.0 mm is formed between the outer bottom portion 22 and the inner bottom portion 32.

Figure 3:
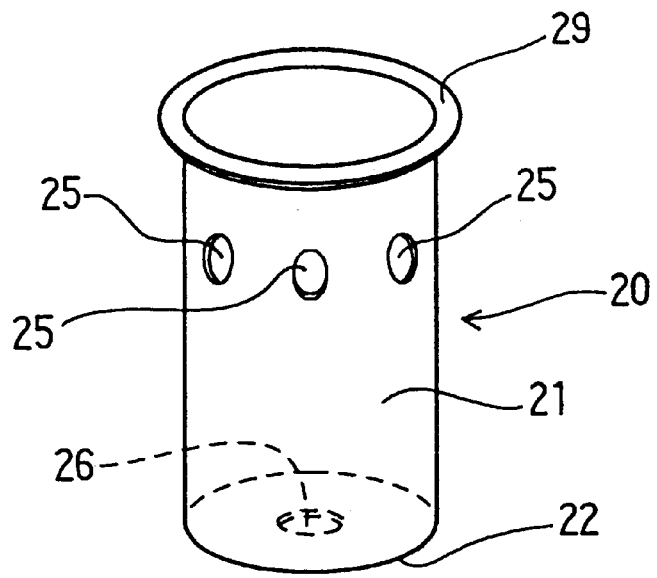
FIG. 3 is a perspective view showing an outer pipe of the element cover according to the first embodiment.

Next, the outer pipe 20 and the inner pipe 3 will be described in detail. As shown in FIG. 3, the outer pipe 20 is formed into a cylindrical shape with a bottom at one end, and has an outer diameter of 12 mm and a longitudinal length of 20 mm. The outer pipe 20 also has a flange portion 29 at an open end thereof, and is fastened to the housing 4 by the flange portion 29. The outer pipe 20 has eight outer side holes 25 arranged in a circumferencial direction thereof. Each of the outer side holes 25 is formed into a circular hole with a diameter of 2 mm. The outer side holes 25 are disposed more adjacent to an open end of the outer pipe 20 or the inner pipe 3 than the inner side holes 35 so that the outer side holes 25 do not overlap the inner side holes 35. The outer bottom hole 26 is formed into a circular hole with a diameter of 1.5 mm at a center of the outer bottom portion 22.

Figure 4:
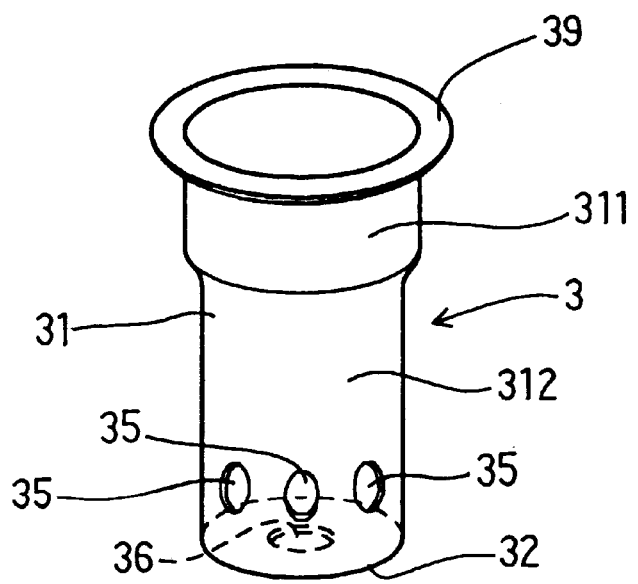
FIG. 4 is a perspective view showing an inner pipe of the element cover according to the first embodiment.

As shown in FIG. 4, the inner pipe 3 is formed into a cylindrical shape with a bottom at one end, and has a longitudinal length of 19.5 mm. The inner side portion 31 has a large diameter portion 311 with an outer diameter of 11 mm and a small diameter portion 312 with an outer diameter of 9 mm. The inner pipe 3 also has a flange portion 39 at an open end thereof, and is fastened to the housing 4 through the flange portion 39. An outer diameter of the flange portion 39 is the same as that of the flange portion 29 of the outer pipe so that the flange portion 29 overlaps the flange portion 39 with a whole area thereof when layered. The inner side portion 31 has eight inner side holes 35 arranged in a circumferencial direction thereof. Each of the inner side holes 35 is formed into a circular hole with a diameter of 2 mm. The inner side holes 35 are disposed more adjacent to the outer and inner bottom portions 22, 32 than the outer side holes 25 so that the inner side holes 35 do not overlap the outer side holes 25. The single inner bottom hole 36 is formed into a circular hole with a diameter of 1.5 mm, and is disposed at a center of the inner bottom portion 32 to overlap the outer bottom hole 26.

As shown in FIG. 2, the gas sensing element 10 is formed into a cup-shape and has a reference gas chamber 12 which contacts atmospheric gas. A sample gas chamber 13 is formed outside the gas sensing element 10 around the gas contact portion 11 in the inner pipe 3. The gas sensing element 10 has a reference electrode (not shown) in the reference gas chamber 12, and a measuring electrode (not shown) in the sample gas chamber 13. Further, a heater 5 for heating the gas sensing element 10 to an appropriate temperature is inserted into the gas sensing element 10.

Referring back to FIG. 1, covers 421, 422 and 423 are disposed at an upper portion of the housing 4 adjacent to atmospheric air. An elastic insulation member 45 is disposed at an upper end of the cover 423. Leads 471, 481 and 491 are inserted into the elastic insulation member 45. An output signal from the gas sensing element 10 is output to outside of the gas sensor 1 through the leads 481, 491. The lead 471 is used for supplying power to the heater 5. Lower ends of the leads 481, 491 in FIG. 1 are respectively connected to connection terminals 482, 492. The connection terminals 482, 492 are respectively connected to metal terminals 483, 493 fastened to the gas sensing element 10. The metal terminals 483, 493 are fastened to each of terminals connected to the reference electrode and the measuring electrode in the gas sensing element 10.

According to the first embodiment, the gas sensor 1 has the double-pipe structure element cover 2 having the outer pipe 20 and the inner pipe 3. The outer side holes 25 and the inner side holes 35 are disposed not to overlap each other. Therefore, the sample gas 8 introduced from the outer side holes 25 into the element cover 2 does not directly contact the gas sensing element 10, but contacts the inner side portion 31. Thereafter, the sample gas 8 flows through the inner side holes 35 toward the gas contact portion 11. As a result, even when the sample gas 8 includes condensed water, condensed water is prevented from directly contacting the gas sensing element 10 and breaking the gas sensing element 10.

Further, according to the first embodiment, the inner side holes 35 are disposed more adjacent to the outer and inner bottom portions 22, 32 than the outer side holes 25. Therefore, as shown in FIG. 2, a flow direction of the sample gas 8 from the outer side holes 25 to the inner side holes 35 coincides with a flow direction of the sample gas 8 from the inner side holes 35 to the inner bottom hole 36 via the gas sensing element 10. As a result, the sample gas 8 flows more smoothly in the element cover 2, and response of the gas sensor 1 is improved.

Further, in the first embodiment, the spacing D is formed between the outer bottom portion 22 and the inner bottom portion 32. Therefore, condensed water adhered to the inner side portion 31 drops downwardly between the outer side portion 21 and the inner side portion 31, flows through the spacing D and is discharged from the outer bottom hole 26. Thus, condensed water can be discharged through the spacing D. Furthermore, in the first embodiment, the spacing D is relatively small as 0.2–1.0 mm. Therefore, flowing resistance of the sample gas 8 in the spacing D is relatively large. As a result, as shown in FIG. 2, the sample gas 8 introduced into a space between the outer pipe 20 and inner pipe 3 tends to flow into the inner side holes 35 rather than into the spacing D. As a result, the sample gas 8 is sufficiently and quickly introduced toward the gas contact portion 11, and response of the gas sensor 1 is improved.

In the first embodiment, the spacing D is set to 0.2–1.0 mm. When the spacing D is larger than 1.0 mm, a relatively large amount of the sample gas 8 introduced into the element cover 2 through the outer side holes 25 flows through the spacing D and is discharged from the outer bottom hole 26. As a result, an amount of the sample gas 8 introduced to the gas contact portion 11 is decreased. On the other hand, when the spacing D is lower than 0.2 mm, condensed water in the space between the outer pipe 20 and the inner pipe 3 may not be discharged.

Further, in the first embodiment, as shown in FIG. 2, outside the gas sensor 1, the sample gas 8 flows substantially perpendicularly to the outer and inner side portions 21, 31. Therefore, the sample gas 8 flowing outside the gas sensor 1 near the outer and inner bottom portions 22, 32 draws the sample gas 8 flowing inside the element cover 2 from the outer and inner bottom holes 36, 26. Since flow resistance in the spacing D is relatively high, an amount of the sample gas 8 drawn from the sample gas chamber 13 is larger than an amount of the sample gas 8 drawn from the spacing D. As a result, a displacement rate of the sample gas 8 in the sample gas chamber 13 is increased, and response of the gas sensor 1 is improved.

(Second Embodiment)

A second preferred embodiment of the present invention will be described with reference to FIGS. 5–11.

Figure 5:
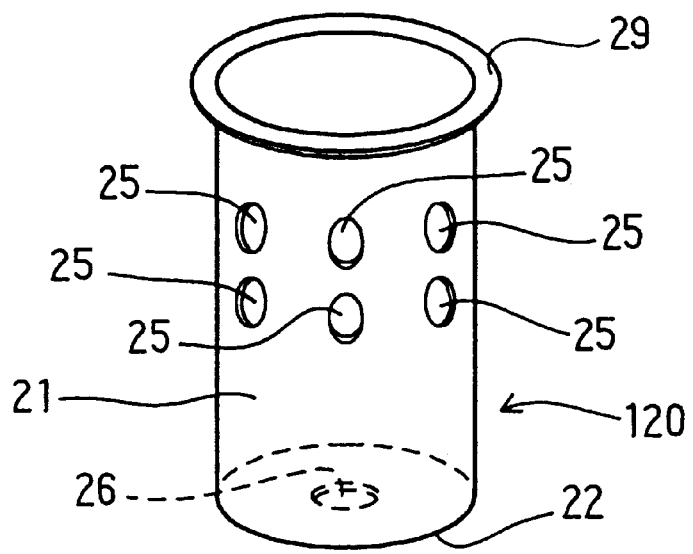
FIG. 5 is a perspective view showing an outer pipe of an element cover of a gas sensor according to a second preferred embodiment of the present invention.
Figure 6:
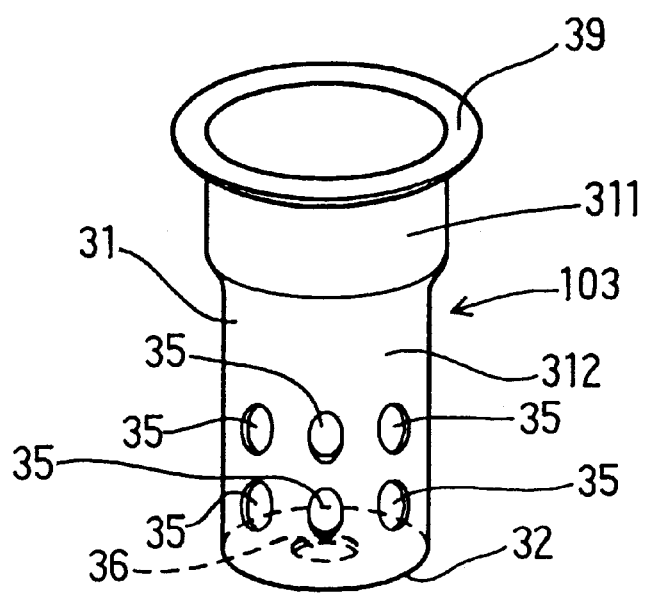
FIG. 6 is a perspective view showing an inner pipe of the element cover according to the second embodiment.

In the second embodiment, each number of the outer and inner side holes 25, 35 is changed. As shown in FIG. 5, an outer pipe 120 has sixteen outer side holes 25 arranged in two rows each of which includes eight holes 25 and extends in a circumferencial direction of the outer pipe 120. That is, the number of the outer side holes 25 in the second embodiment is increased by eight from that in the first embodiment. Further, as shown in FIG. 6, an inner pipe 103 has sixteen inner side holes 35 arranged in two rows each of which includes eight holes 35 and extends in a circumferencial direction of the inner pipe 103. That is, the number of the inner side holes 35 in the second embodiment is also increased by eight from that in the first embodiment. The outer side holes 25 and the inner side holes 35 do not overlap each other, and the inner side holes 35 are disposed more adjacent to the outer and inner bottom portions 22, 32 than the outer side holes 25.

According to the second embodiment, a flow speed of the sample gas 8 is further increased due to increase in the number of the outer and inner side holes 25, 35. As a result, response of the gas sensor 1 is further improved. However, when each number of the outer and inner side holes 25, 35 is increased, foreign matters such as condensed water tend to be introduced into the gas sensor 1 more readily. Therefore, the outer side holes 25 and the inner side holes 35 need to be disposed not to overlap each other.

Figure 7:
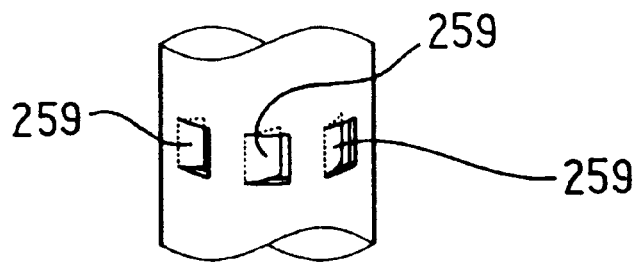
FIG. 7 is a perspective view showing partially side holes formed in the element cover according to a modification of the second embodiment.

Each number and arrangement of the outer and inner side holes 25, 35 may be changed as long as the outer side holes 25 and the inner side holes 35 do not overlap each other. Further, each of the holes 25, 26, 35 and 36 is not limited to a circular shape, but may be formed into any other shape. For example, as shown in FIG. 7, each of the holes 25, 26, 35 and 36 may be formed by cutting and raising a cut portion 259 like a louver.

Next, a relationship between the spacing D and response of the gas sensor 1 was examined to quantitatively evaluate effects on response of the gas sensor 1 in the first and second embodiments. The gas sensors 1 with the spacing D of 0.1, 0.3, 0.5, 0.75, 1.0 and 1.7 mm were prepared. The element cover 2 was prepared according to the second embodiment.

Figure 8:
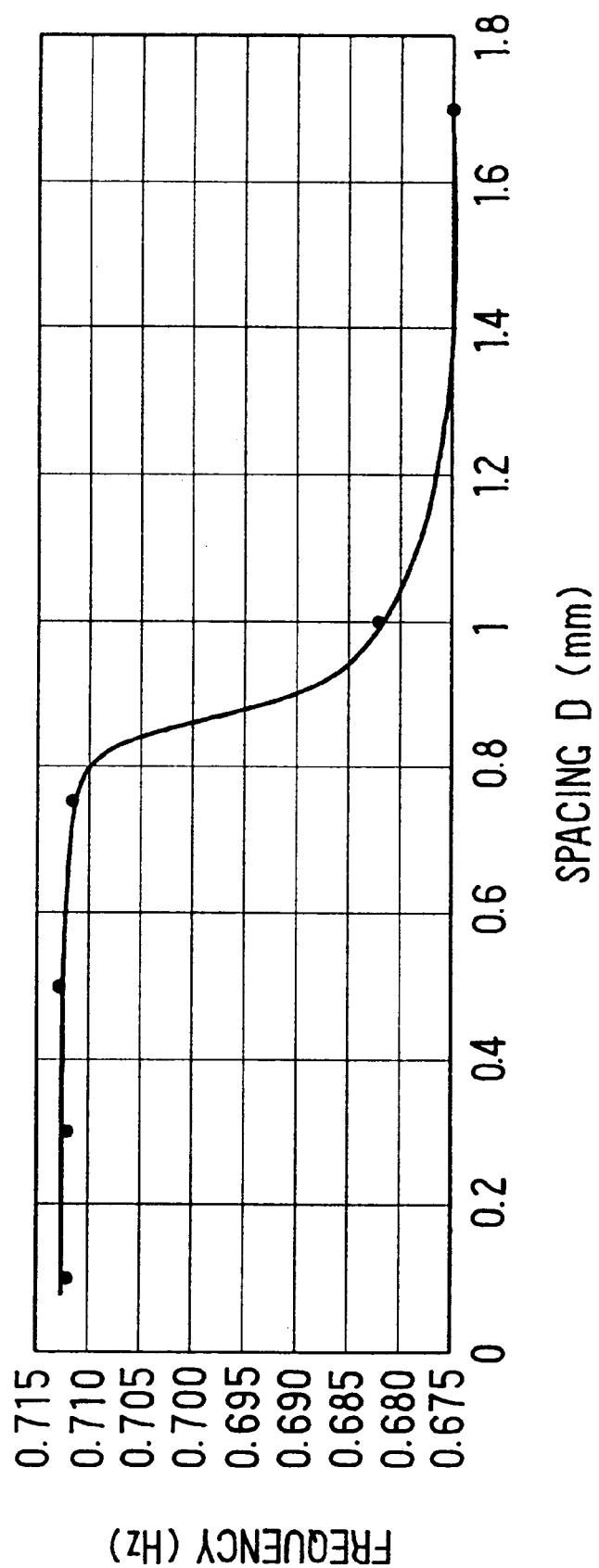
FIG. 8 is a graph showing a relationship between a spacing D and sensor output frequency of the gas sensor according to the second embodiment.

The gas sensor 1 was attached to an exhaust gas pipe of an in-line six-cylinder injection type gasoline engine with a displacement volume of 2,000 cc, and output of the gas sensor 1 was measured. The gasoline engine was operated at 1,100 rpm using unleaded gasoline. Output frequency (i.e., frequency feed back or FFB) of the gas sensor 1 when the engine was operated at 1,100 rpm was measured. The results are shown in FIG. 8. In FIG. 8, a unit of output frequency is number of cycles for one second and is represented by Hz.

Figure 9:
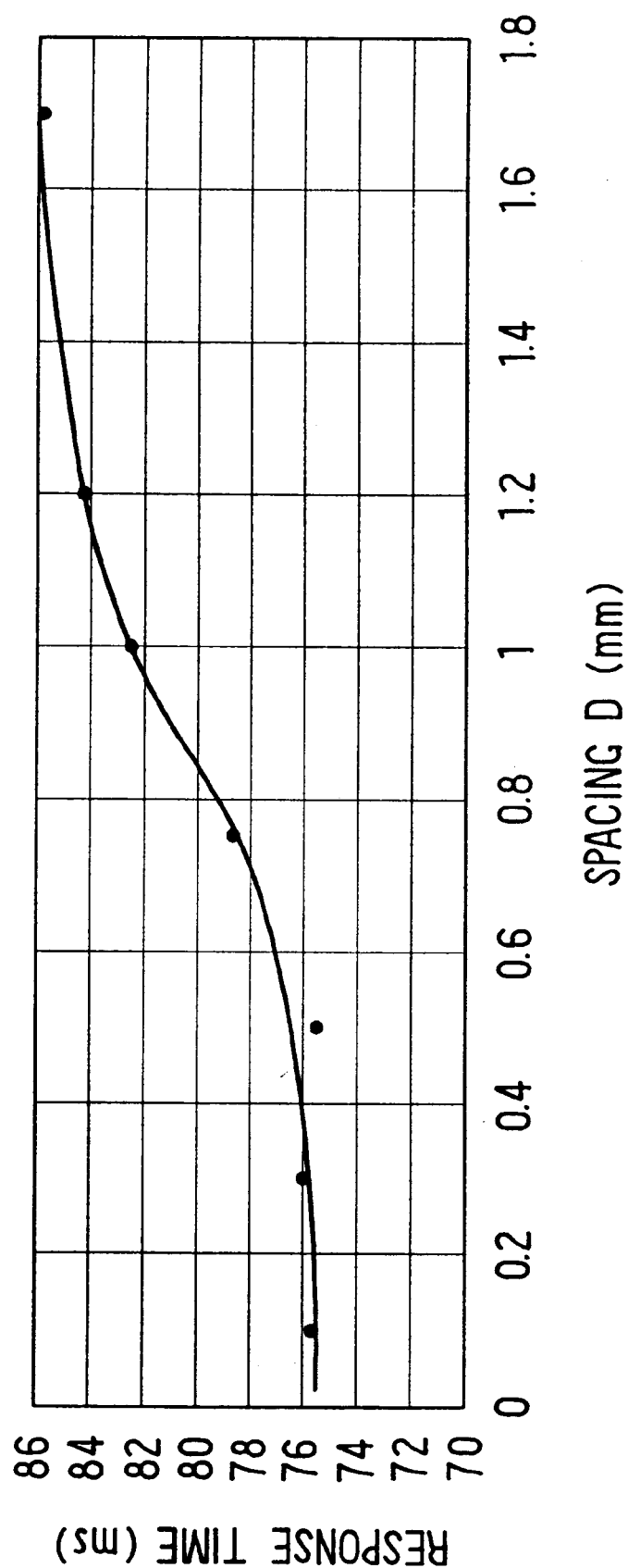
FIG. 9 is a graph showing a relationship between the spacing D and response time of the gas sensor during a rich to lean transition according to the second embodiment.
Figure 10:
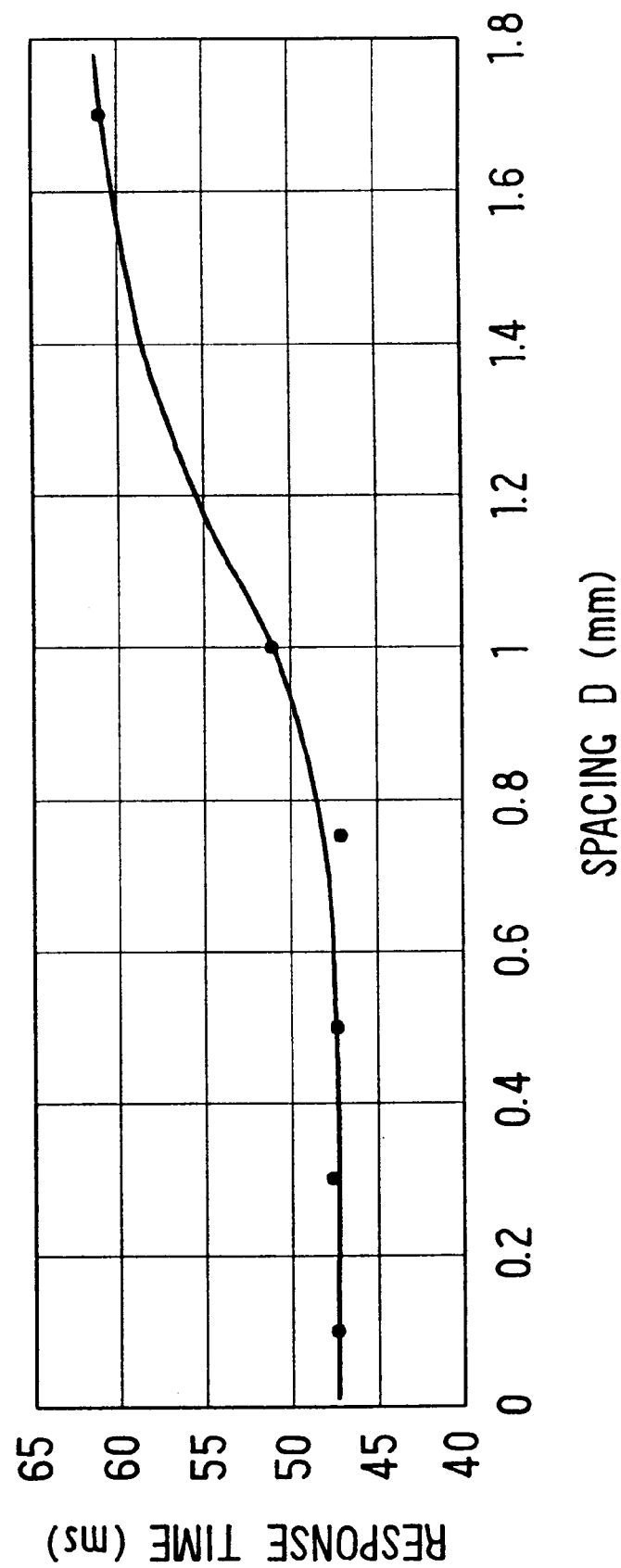
FIG. 10 is a graph showing a relationship between the spacing D and response time of the gas sensor during a lean to rich transition according to the second embodiment.

When an air-fuel mixture ratio is 14.7 (i.e., a ratio of air to fuel by weight is 14.7 to 1), the air-fuel mixture ratio is represented by $\lambda$. Response of the gas sensor 1 was measured during a period while the air fuel mixture ratio changed from $\lambda 0.9$ to $\lambda 1.1$, i.e., from rich air-fuel mixture to lean air-fuel mixture (hereinafter referred to as rich to lean transition), and the results are shown in FIG. 9. Response of the gas sensor 1 was measured during a period while air fuel mixture ratio changed from $\lambda 1.1$ to $\lambda 0.9$, i.e., from lean air-fuel mixture to rich air-fuel mixture (hereinafter referred to as lean to rich transition), and the results are shown in FIG. 10. Response of the gas sensor 1 during the rich to lean transition was estimated from time elapsing while output of the gas sensor 1 changed from 0.6 V to 0.3 V. Response of the gas sensor 1 during the lean to rich transition was estimated from time elapsing while output of the gas sensor 1 changed from 0.3 V to 0.6 V. The results are shown in TABLE 1.

TABLE 1

| Spacing D | Frequency | Response time (ms) | |
|---|---|---|---|
| (mm) | (Hz) | Rich to lean | Lean to rich |
| 0.1 | 0.712 | 75.6 | 47.3 |
| 0.3 | 0.712 | 76 | 47.5 |
| 0.5 | 0.713 | 75.5 | 47.3 |
| 0.75 | 0.712 | 78.7 | 47.2 |
| 1 | 0.682 | 82.4 | 51.3 |
| 1.7 | 0.675 | 85.8 | 61 |

As shown in TABLE 1 and FIGS. 8–10, when the spacing D is 1.0 mm or lower, especially 0.8 mm or lower, the gas sensor 1 has excellent response with respect to both frequency and response time. However, when the spacing D is 0.2 mm or lower, although the gas sensor 1 has a good response, condensed water entering between the outer pipe 120 and the inner pipe 103 may not be smoothly discharged. As a result, condensed water may enter the inside pipe 103 and break the gas sensing element 10. Therefore, the spacing D is preferably set to 0.2–1.0 mm.

Figure 11:
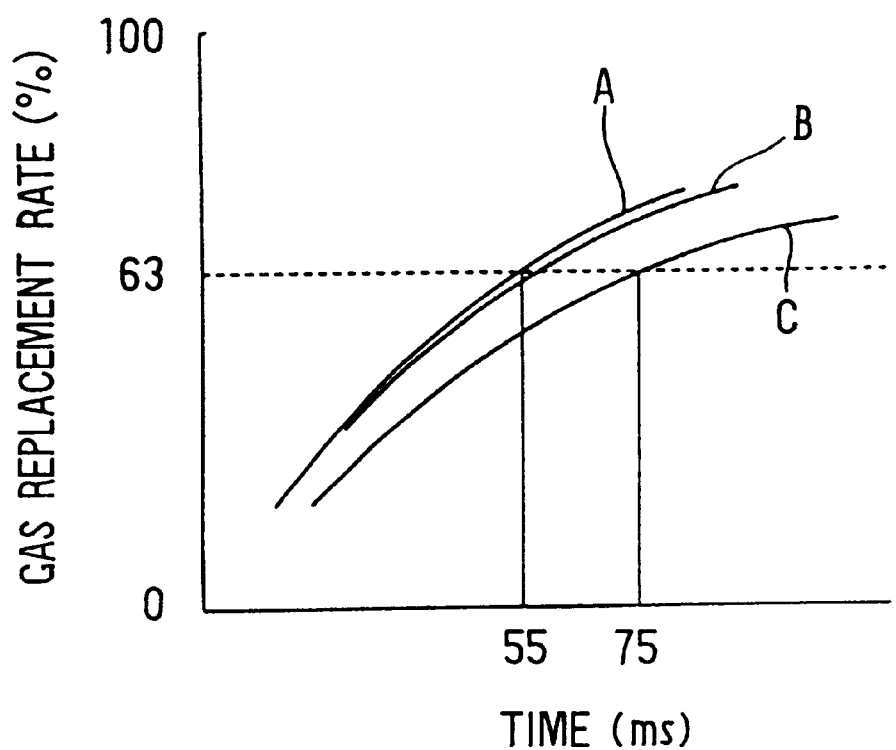
FIG. 11 is a graph showing a relationship between elapsed time and a gas displacement rate of each of the gas sensors having the spacing D of 0, 0.5 and 1.0 mm according to the second embodiment.

Next, a gas displacement rate in the sample gas chamber 13 of each of the gas sensors 1 with the spacing D of 0, 0.5 and 1.0 mm was estimated by a finite-element method (FEM). The results are shown in FIG. 11. In FIG. 11, time is plotted on a horizontal axis and the gas displacement rate is plotted on a vertical axis. Lines A, B and C respectively represent the gas sensors 1 with the spacing D of 0, 0.5 and 1.0 mm.

As shown in FIG. 11, when the spacing D is 1.0 mm, time elapsing until the gas displacement rate reaches 63% is 75 ms. Thus, when the spacing D is 1.0 mm or lower, gas is replaced very quickly, thereby improving response of the gas sensor 1. Although the gas sensor 1 with the spacing D of 0.2 mm or lower has good response, it has the above-mentioned drainage problem of condensed water. Therefore, the spacing D is preferably set to 0.2–1.0 mm.

(Third Embodiment)

Figure 12A:
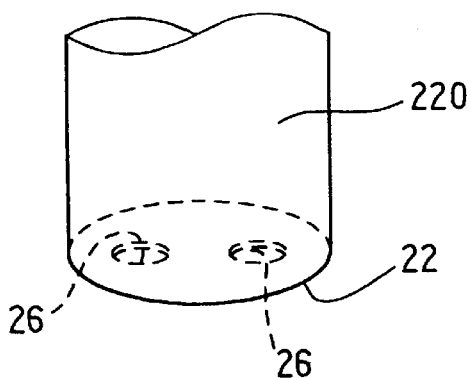
FIG. 12A is a perspective view showing partially an outer pipe of an element cover of a gas sensor having two outer bottom holes according to a third preferred embodiment of the present invention.
Figure 12B:
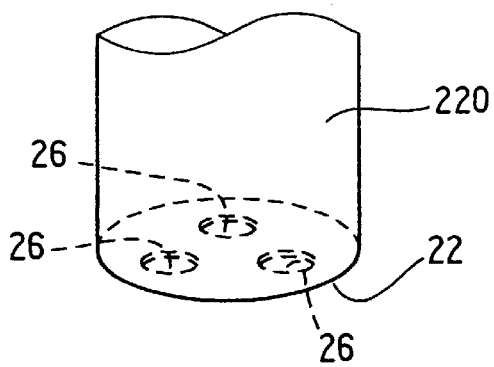
FIG. 12B is a perspective view showing partially the outer pipe having three outer bottom holes according to the third embodiment.

A third preferred embodiment of the present invention will be described with respect to FIGS. 12A and 12B. In the third embodiment, the number and arrangement of the outer bottom holes 26 are changed. In FIG. 12A, the number of the outer bottom holes 26 of an outer pipe 220 is increased to two. In FIG. 12B, the number of the outer bottom holes 26 is increased to three, and the outer bottom holes 26 are arranged so that each of the holes 26 is disposed at each vertex of a triangle. The inner bottom hole 36 is disposed at the center of the inner bottom portion 32 same as in the first embodiment.

According to the third embodiment, the plural outer bottom holes 26 are disposed not to overlap the inner bottom hole 36. Therefore, condensed water or the like is prevented from flowing back into the gas sensor 1 through the inner and outer bottom holes 26, 36. The number of the inner bottom hole 36 may be increased to two or more while the number of the outer bottom hole 26 is one.

(Fourth Embodiment)

A fourth preferred embodiment of the present invention will be described with reference to FIGS. 13A–13C. In the fourth embodiment, the outer bottom portion 22 and the inner bottom portion 32 are deformed.

Figure 13A:
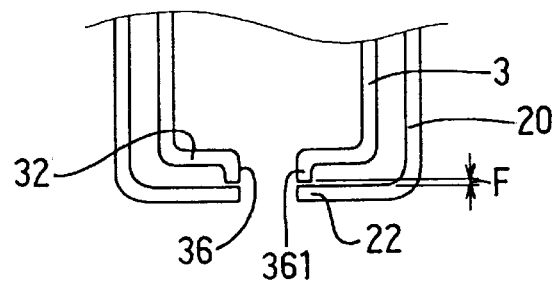
FIGS. 13A–13C are explanatory views each showing a structure of a bottom portion of an element cover of a gas sensor according to a fourth preferred embodiment of the present invention.

In FIG. 13A, the inner bottom portion 32 has a cylindrical protruding portion 361 formed to protrude downwardly along a circumference of the inner bottom hole 36. A spacing F of 0.2–1.0 mm is formed between an protruding end of the protruding portion 361 and the outer bottom portion 22.

Figure 13B:
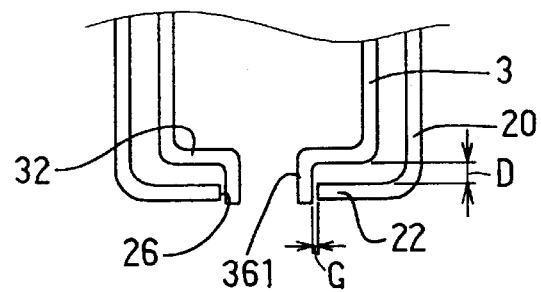

In FIG. 13B, the protruding portion 361 is further extended downwardly to be inserted into the outer bottom hole 26. In this case, a spacing G of 0.2–1.0 mm is formed between an outer circumferencial surface of the protruding portion 361 and an inner circumferencial surface of the outer bottom hole 26.

Figure 13C:
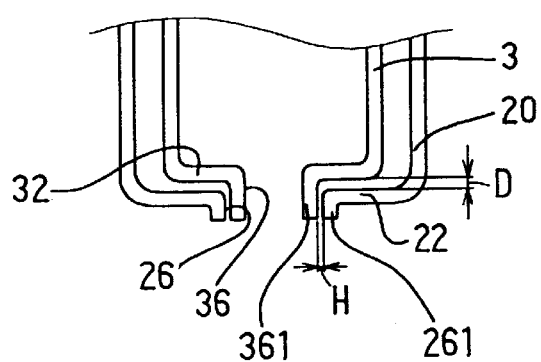

In FIG. 13C, the outer bottom portion 22 has a protruding portion 261 formed to protrude downwardly along a circumference of the outer bottom hole 26. A spacing H of 0.2–1.0 mm is formed between an inner circumferencial surface of the protruding portion 261 and the outer circumferencial surface of the protruding portion 361. In FIGS. 13B and 13C, the spacing D may be set to 0.2–1.0 mm.

In the fourth embodiment, the same effects as in the first embodiment are obtained.

(Fifth Embodiment)

Figure 14:
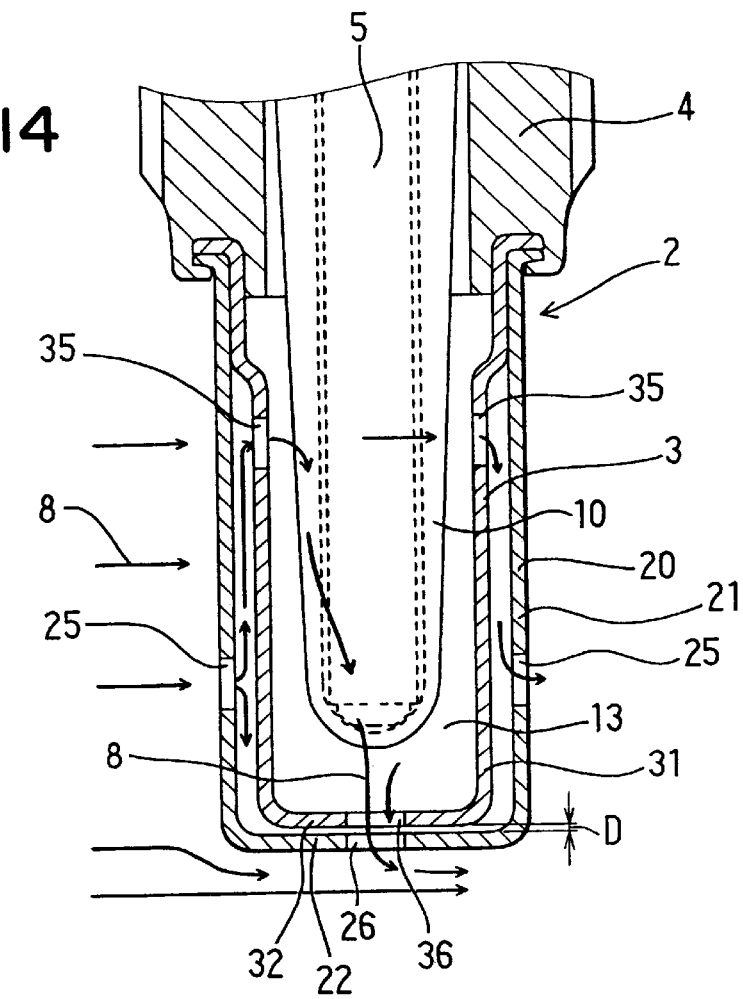
FIG. 14 is a schematic sectional view showing a gas sensing element and an element cover of a gas sensor according to a fifth preferred embodiment of the present invention.

A fifth preferred embodiment of the present invention will be described with reference to FIGS. 14–16. In the fifth embodiment, a positional relation between the outer side holes and the inner side holes 35 is opposite to that in the first embodiment. That is, in the fifth embodiment, as shown in FIG. 14, the outer side holes 25 are disposed more adjacent to the outer and inner bottom portions 22, 32 than the inner side holes 35.

According to the fifth embodiment, a flow direction of the sample gas 8 from the outer side holes 25 to the inner side holes 35 is substantially opposite to a flow direction of the sample gas 8 from the inner side holes 35 to the inner bottom hole 36 through the gas sensing element 10. Therefore, condensed water or the like entering the element cover 2 through the outer side holes 25 along with the sample gas 8 tends to be accumulated between the outer pipe 20 and the inner pipe 3 when the sample gas 8 changes its flow direction in the inner side holes 35. As a result, condensed water or the like is further prevented from entering inside of the gas sensor 1.

Next, a gas replacement rate in each sample gas chamber 13 of the gas sensor 1 according to the first embodiment (E1) and the gas sensor 1 according to the fifth embodiment (E5) was estimated by FEM. The results are shown in FIG. 15. In FIG. 15, elapsed time is plotted on a horizontal axis and the gas replacement rate is plotted on a vertical axis.

Figure 15:
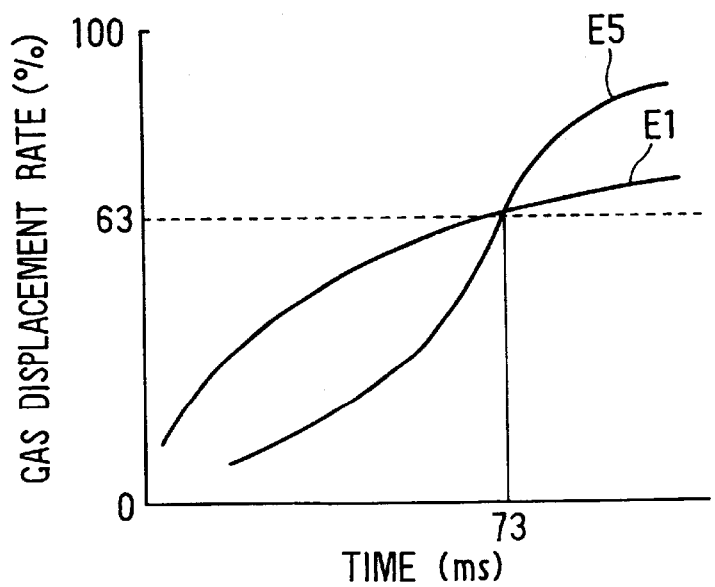
FIG. 15 is a graph showing a relationship between elapsed time and a gas replacement rate of the gas sensor according to the first and fifth embodiments.

As shown in FIG. 15, time elapsing until the gas displacement rate of E1 to reach 63% is equal to that of E5. However, when the elapsed time is less than 73 ms, the gas replacement rate of E1 is larger than that of E5, and after the elapsed time exceeds 73 ms, the gas replacement rate of E5 is larger than that of E1. Therefore, it is preferable to use either E1 or E5 depending on conditions such as an attachment position of the gas sensor 1 to make use of these differences in characteristics between E1 and E5.

Next, a relationship among a diameter d of each inner and outer bottom holes 36, 26, the spacing D and response of the gas sensor 1 according to the fifth embodiment was examined. Sensor output frequency (FFB) of the gas sensor 1 when the engine was operated at 1,100 rpm was measured in the same method in the second embodiment. The results are shown in TABLE 2 and FIG. 16. In FIG. 16, lines Q, R, S and T respectively represent the gas sensors 1 with the distance d of 1, 2, 3 and 4 mm.

TABLE 2

| Spacing D (mm) | Frequency (Hz) | | | |
| --- | --- | --- | --- | --- |
|  | Q (d = 1 mm) | R (d = 2 mm) | S (d = 3 mm) | T (d = 4 mm) |
| 0.1 | — | 0.712 | — | — |
| 0.3 | 0.691 | 0.712 | 0.738 | 0.761 |
| 0.5 | 0.688 | 0.713 | 0.736 | 0.751 |
| 0.75 | — | 0.712 | 0.728 | 0.742 |
| 1 | 0.673 | 0.682 | 0.686 | 0.702 |
| 1.7 | 0.659 | 0.675 | 0.68 | 0.689 |

Figure 16:
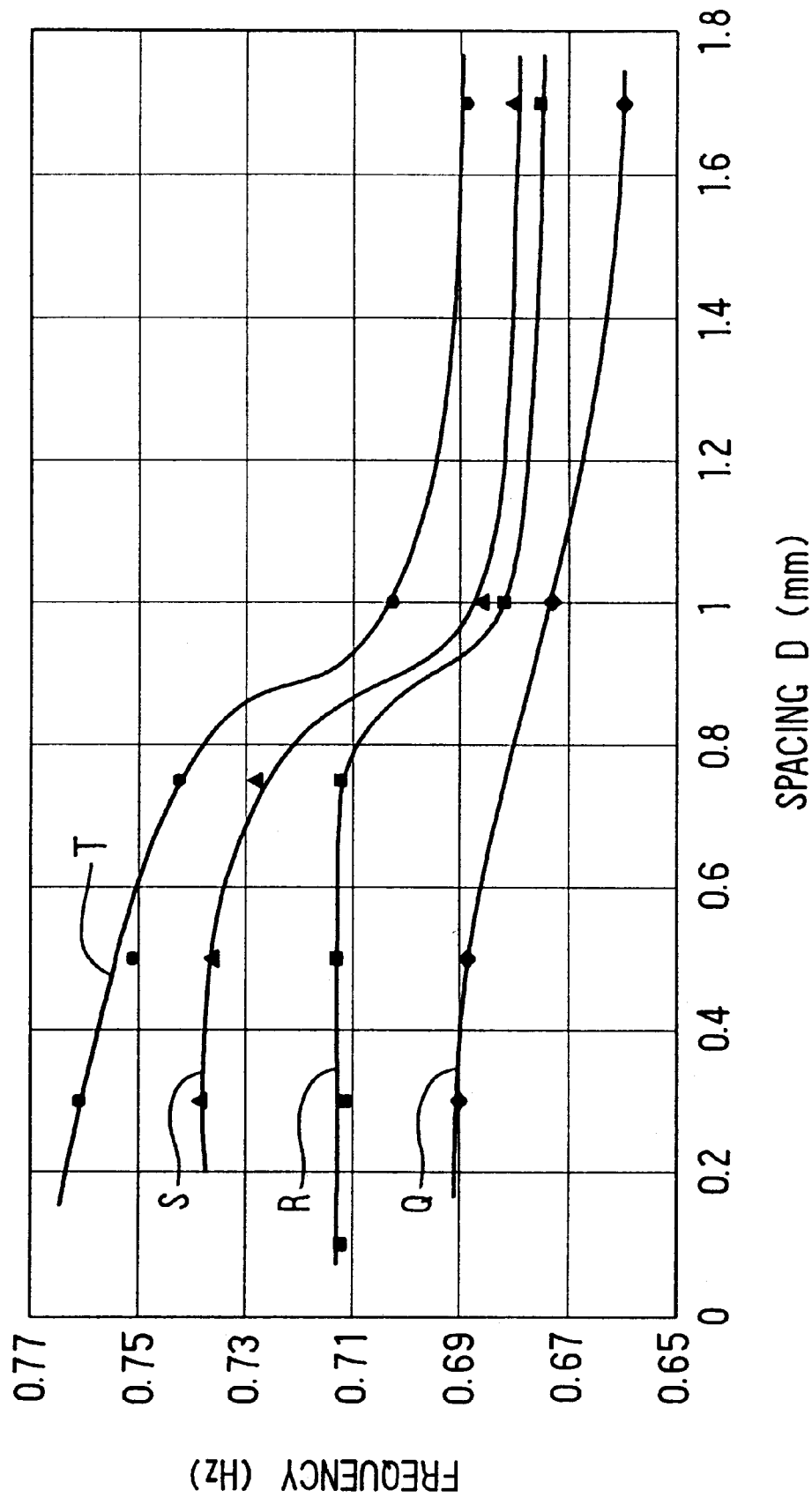
FIG. 16 is a graph showing a relationship between a spacing D and sensor output frequency of each of the gas sensors having a diameter d of 1–4 mm according to the fifth embodiment.

As shown in TABLE 2 and FIG. 16, response of the gas sensor 1 is worsened when the spacing D is larger than 1 mm, irrespective to the diameter d. The gas sensor 1 has excellent response when the spacing D is 0.8 mm or lower. However, when the diameter d becomes smaller, introduction and discharge of the sample gas through the outer and inner bottom holes 26, 36 also becomes difficult.

It is known that the diameter d is preferably set to 0.5–5 mm from TABLE 2 and FIG. 16. When the diameter d is less than 0.5 mm, introduction and discharge of the sample gas through the outer and inner bottom holes 26, 36 becomes difficult. When the diameter d is larger than 5 mm, condensed water in the sample gas readily reaches the sensing element 101. More preferably, the diameter d is set to 1–4 mm.

(Sixth Embodiment)

A sixth preferred embodiment of the present invention will be described with reference to FIGS. 17–20. In the sixth embodiment, the gas sensor 1 has a layered type oxygen sensing element 101.

Figure 17:
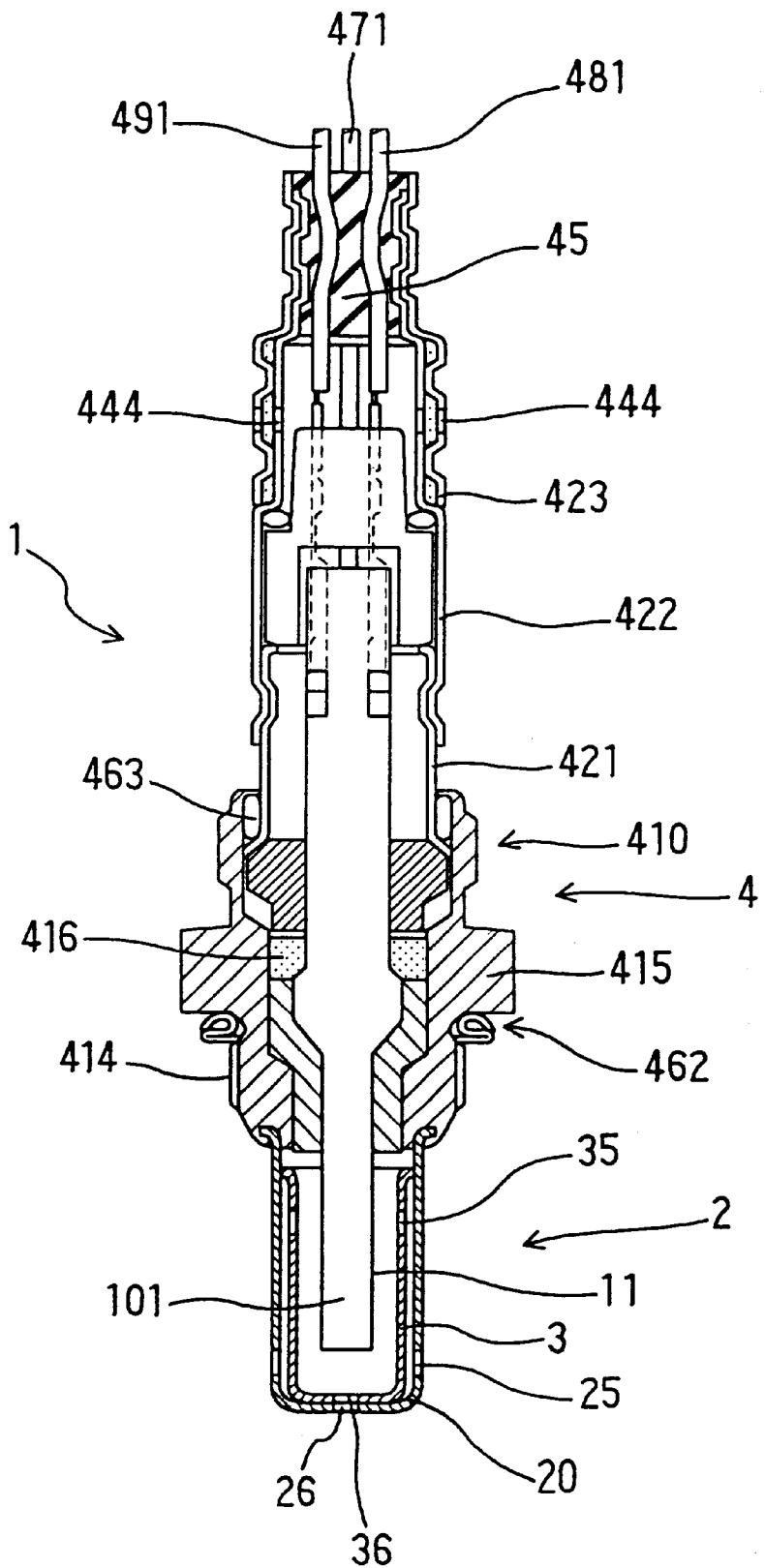
FIG. 17 is a schematic sectional view showing a gas sensor according to a sixth preferred embodiment of the present invention.

As shown in FIG. 17, the gas sensor 1 has the layered type oxygen sensing element 101 having the gas contact portion 11 made of solid electrolyte, the housing 4 for holding the oxygen sensing element 101 and the element cover 2 covering the end portion of the gas contact portion 11 and including the inner pipe 3 and the outer pipe 20, similarly to the first to fifth embodiments.

Figure 18A:
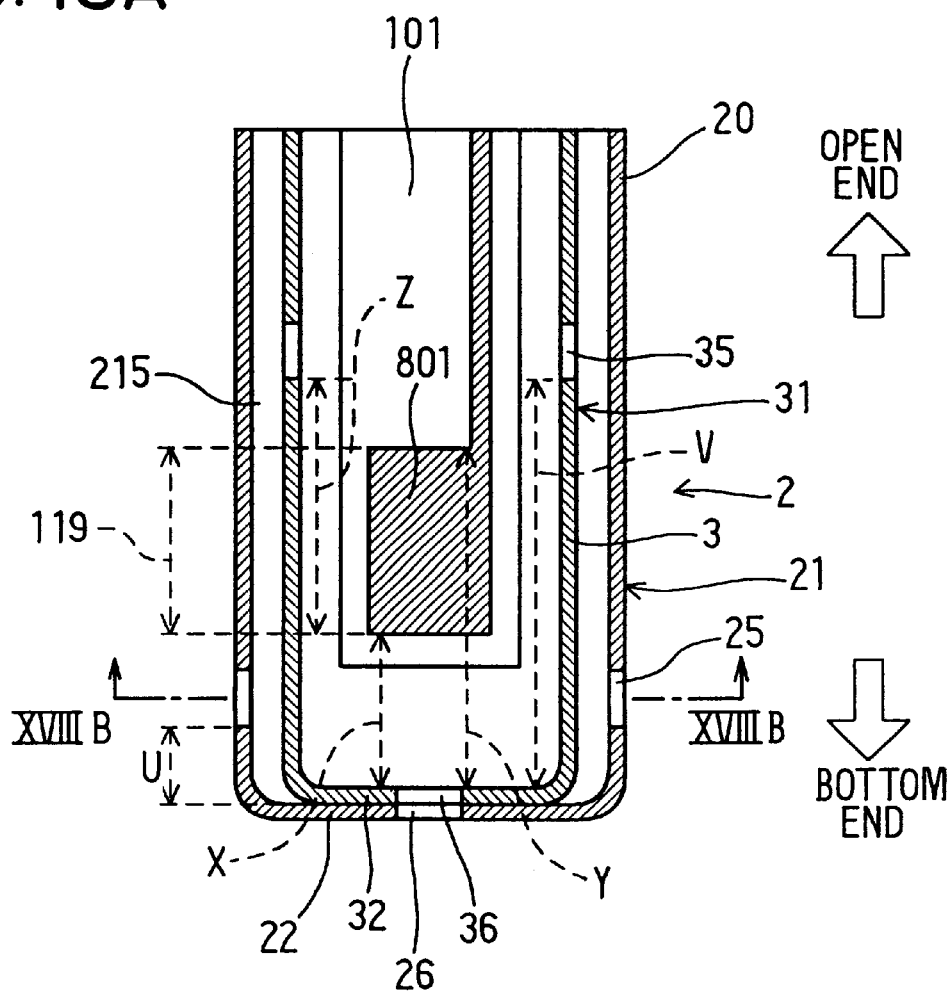
FIG. 18A is a schematic sectional view showing an oxygen sensing element and an element cover of the gas sensor according to the sixth embodiment.
Figure 18B:
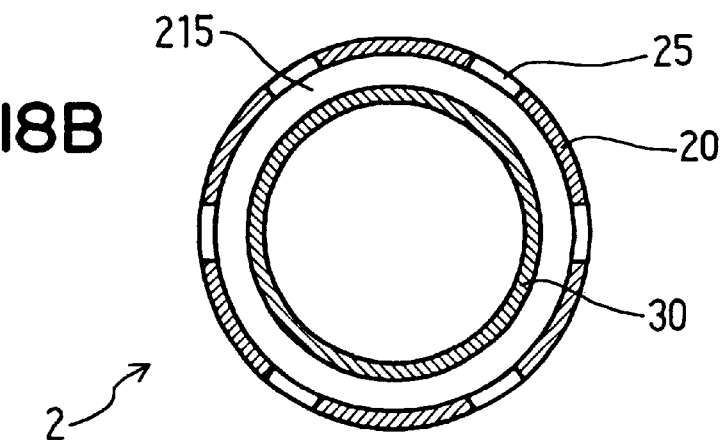
FIG. 18B is a sectional view taken along line XVIIIB—XVIIIB in FIG. 18A.

As shown in FIGS. 18A and 18B, the outer pipe 20 has six outer side holes 25 arranged in a row extending perpendicularly to a center axis of the oxygen sensing element 101. A distance U between the outer bottom portion 22 and a lower end of the outer side holes 25 in FIG. 18A is 4 mm. Each of the outer side holes 25 is a circular hole with a diameter of 2 mm. The outer bottom hole 26 is disposed at a center of the outer bottom portion 22, and is formed into a circular hole with a diameter of 2 mm. Further, the inner side portion 31 has six inner side holes 35 arranged in a row extending perpendicularly to a center axis of the oxygen sensing element 101. A distance V between the inner bottom portion 32 and a lower end of the inner side holes 35 in FIG. 18A is 15 mm. Each of the inner side holes 35 is a circular hole with a diameter of 2 mm. The inner bottom hole 36 is disposed at a center of the inner bottom portion 32, and is formed into a circular hole with a diameter of 2 mm. A space 215 is formed between the inner side portion 31 and the outer side portion 21.

The oxygen sensing element 101 has a gas sensing portion 119. A distance X between a lower end of the gas sensing portion 119 in FIG. 18A and the inner bottom portion 32 is 6 mm. A distance Y between an upper end of the gas sensing portion 119 in FIG. 18A and the inner bottom portion 32 is 10 mm. Therefore, in the sixth embodiment, the inner side holes 35 are disposed more adjacent to an opening end of the element cover 2 than the gas sensing portion 119. Further, the outer and inner bottom portions 22 and 32 are joined to each other by spot welding so that the outer bottom hole 26 overlaps the inner bottom hole 36.

In the sixth embodiment, the gas sensor 1 is an air-fuel mixture ratio sensor for detecting an air-fuel mixture ratio of a vehicle engine. As shown in FIG. 17, a body portion 410 of the housing 4 has a screw portion 414 for engaging with a screw hole formed in an exhaust gas passage (not shown) of the vehicle engine, and a flange portion 415 for contacting the exhaust gas passage. Each of the cover portions 422, 423 has plural atmospheric air inlets 444 through which atmospheric air is introduced to the oxygen sensing element 101. Powder 416 is disposed between the oxygen sensing element 101 and the body portion 410 so that the oxygen sensing element 101 is held by the body portion 410 through the powder 416. Further, a gasket 462 and a metal ring 463 are provided as shown in FIG. 17.

Figure 19:
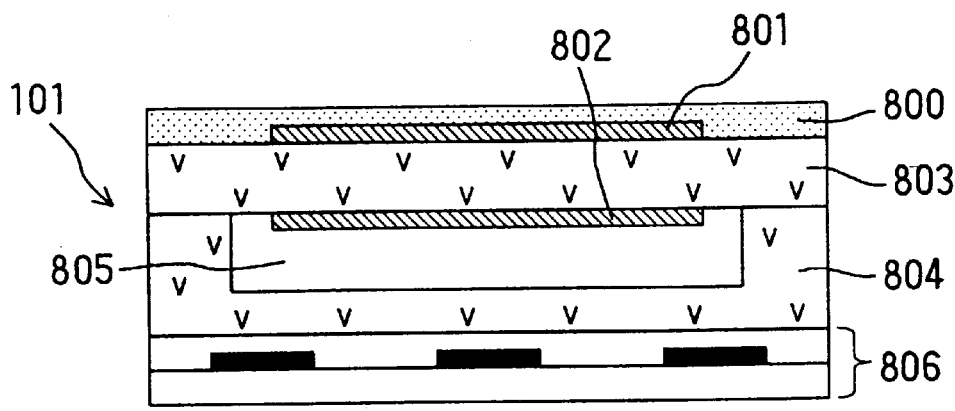
FIG. 19 is a schematic sectional view showing the oxygen sensing element according to the sixth embodiment.

As shown in FIG. 19, the oxygen sensing element 101 is formed by disposing electrodes 801, 802 on a solid electrolyte plate 803 so that the electrode 801 is disposed on one surface of the plate 803 and the electrode 802 is disposed on the other surface of the plate 803. The electrode 801 contacts the sample gas through a protection layer 800. The electrode 802 faces an atmospheric room 805 formed by a spacer 804. Further, the oxygen sensing element 101 has a heater portion 806 integrally formed. The heater portion 806 has a heating electrical wire (not shown) connected to the lead 471. The gas sensing portion 119 represents an area where the electrode 801 exists.

According to the sixth embodiment, as shown in FIG. 18A, a part of the sample gas introduced through one of the outer side holes 25 is discharged from another one of the outer side holes 25, and the rest of the sample gas is introduced into the inner pipe 3 through the inner side holes 35. The sample gas introduced into the inner pipe 3 passes through the gas sensing portion 119 and is discharged from the inner and outer bottom holes 36, 26.

A conventional gas sensor having a layered type gas sensing element has an element cover which decreases fluctuation in response of the gas sensor even if a relation between a flow direction of the sample gas and an axial direction of the gas sensing element changes. However, according to simulation of gas flow in the above-mentioned element cover conducted by the inventors, gas flows only within a plane perpendicular to an axis of the gas sensing element when the element cover has plural side holes arranged in plural rows. Therefore, response of the gas sensor changes when an attachment direction of the gas sensing element changes.

According to the sixth embodiment, a direction of the sample gas in the inner pipe 3 is the same as an axial direction of the oxygen sensing element 101. As a result, the sample gas is well mixed while flowing in the axial direction of the element 101, and a concentration of the sample gas becomes substantially uniform. Therefore, even if an attachment direction of the gas sensor 1 changes, the gas sensor 1 has a constant fast response.

Further, in the sixth embodiment, the outer and inner bottom portions 22, 32 are welded to each other. Therefore, the sample gas introduced through the outer side holes 25 is prevented from being directly discharged through the outer bottom hole 25. As a result, the sample gas flows upwardly in the space 215, and enters the inner pipe 3 through the inner side holes 35. Thereafter, the sample gas is discharged from the element cover 2 through the outer and inner bottom holes 26, 36. Therefore, an amount of the sample gas entering the inner pipe 3 increases, thereby improving response of the gas sensor 1.

The sample gas introduced into the element cover 2 through the outer side holes 25 deprives heat from the inner pipe 3. In the sixth embodiment, the outer side holes 25 are arranged in a single row, and a total opening area of the holes 25 is smaller than that of the holes 25 arranged in plural rows. As a result, power consumption of the heater portion 806 is reduced.

Next, a relationship between a distance Z between the lower end of the gas sensing portion 119 and the lower end of the inner side holes 25 in FIG. 18A and response of the gas sensor 1 was examined as follows.

Figure 20:
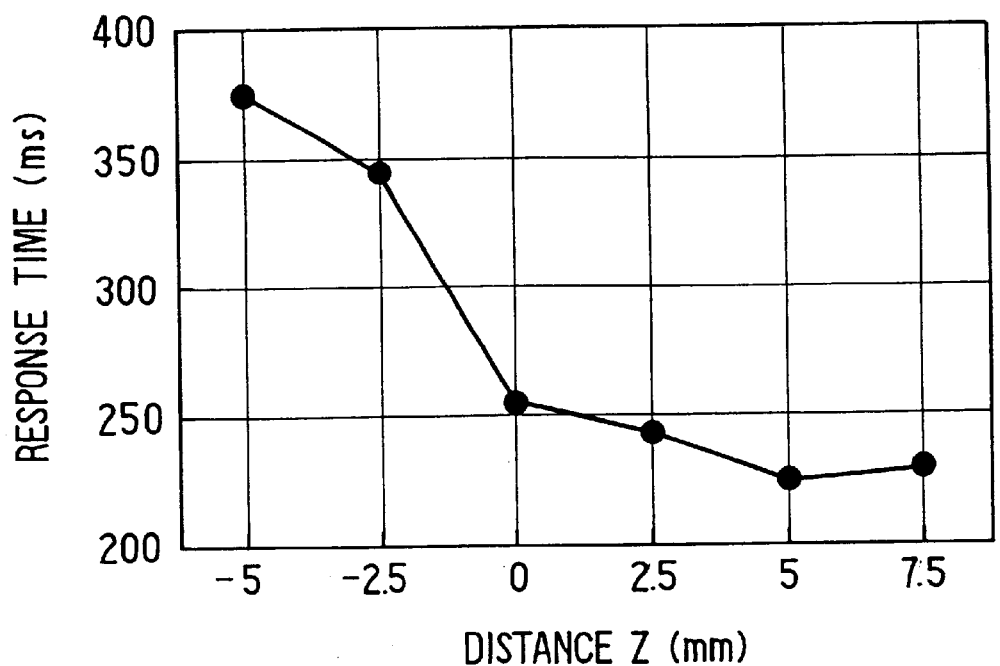
FIG. 20 is a graph showing a relationship between a distance Z and response time of the gas sensor according to the sixth embodiment.

The gas sensor 1 was attached to an exhaust gas pipe of an in-line four-cylinder injection type gasoline engine with a displacement volume of 2,000 cc, and output of the gas sensor 1 was measured. The gasoline engine was operated at 1,500 rpm using unleaded gasoline. Response of the gas sensor 1 when the air-fuel mixture ratio was changed from 14 to 15 was measured as follows. First, output of the gas sensor 1 at the air-fuel mixture ratio of 14 and output of the gas sensor 1 at the air-fuel mixture ratio of 15 were measured. Next, output of the gas sensor 1 was measured while the air-fuel mixture ratio was changed from 14 to 15. Response of the gas sensor 1 was estimated from time elapsing until difference between the output at the air-fuel mixture ratio of 14 and the output at the air-fuel mixture ratio of 15 was decreased by 63%. The results are shown in FIG. 20. In FIG. 20, the distance Z is plotted on a horizontal axis and response time of the gas sensor 1 is plotted on a vertical axis. The distance Z is positive when the lower end of the gas sensing portion 119 is disposed more adjacent to the inner bottom portion 32 than the lower end of the inner side holes 35, and is negative when the lower end of the inner side holes 35 is disposed more adjacent to the inner bottom portion 32 than the lower end of the gas sensing portion 119 in FIG. 18A.

As shown in FIG. 20, when the distance Z becomes smaller, the gas sensor 1 has a longer response time. Therefore, the lower end of the gas sensing portion 119 needs to be disposed more adjacent to the inner bottom portion 32 than the lower end of the inner side holes 35 in FIG. 18A, i.e., the distance z needs to be larger than 0, so that the gas sensor 1 has fast response.

Further, the above-mentioned measurements were performed for the gas sensors 1 having various values of an area of the gas sensing element 119. According to the measurements, the above-mentioned relation between response time and the distance Z is more salient when the gas sensing portion 119 has a smaller area.

In the gas sensor 1 having the cup-shaped gas sensing element 10 according to the first embodiment, a substantially whole area of the gas contact portion 11 corresponds to the gas sensing portion 119. As a result, an area of the gas sensing portion 119 in the first embodiment is larger than that of the sixth embodiment. Therefore, a positional relationship between the inner side holes 35 and the gas sensing portion 119 has little influence on response time of the gas sensor 1 in the first embodiment.

(Seventh Embodiment)

A seventh preferred embodiment of the present invention will be described with reference to FIGS. 21A and 21B. In the seventh embodiment, the element cover 2 in the sixth embodiment is modified.

Figure 21A:
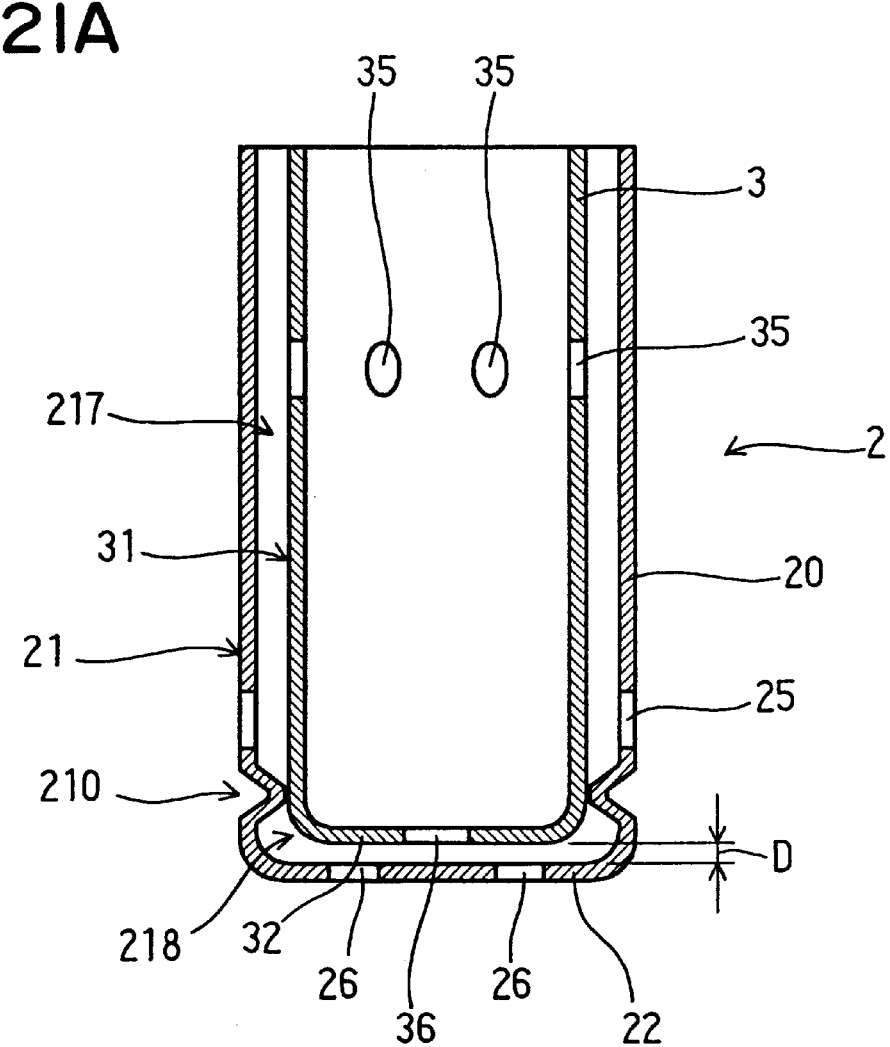
FIG. 21A is a schematic sectional view showing an element cover of a gas sensor according to a seventh preferred embodiment of the present invention.
Figure 21B:
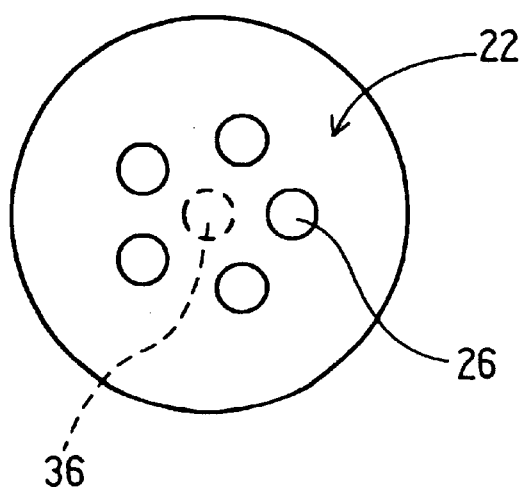
FIG. 21B is a bottom plan view showing a bottom portion of the element cover according to the seventh embodiment.

In the seventh embodiment, as shown in FIG. 21A, the spacing D is set to 1 mm. As shown in FIG. 21B, the inner bottom hole 36 is a circular hole with a diameter of 2 mm, and is disposed at a center of the inner bottom portion 32. Five outer bottom holes 26 are disposed along a circumference of a circle having a center aligned with the center of the outer bottom portion 22 and a diameter of 4 mm. Each of the outer bottom holes 26 is a circular hole with a diameter of 1.5 mm.

Further, as shown in FIG. 21A, the outer side portion 21 has a recess portion 210 in the vicinity of the outer bottom portion 22. As a result, a space between the inner pipe 3 and the outer pipe 20 is partitioned into a side space 217 and a bottom space 218 by the recess portion 210, thereby restricting the sample gas from flowing between the side space 217 and the bottom space 218.

According to the seventh embodiment, due to the recess portion 210, the sample gas introduced into the element cover 2 through the outer side holes 25 is restricted from being directly discharged from the outer bottom holes 26, but flows upwardly in the side space 217 and enters the inner pipe 3 through the inner side holes 35. Thereafter, the sample gas is discharged from the element cover 2 through the inner and outer bottom holes 36, 26. Therefore, an amount of the sample gas entering the inner pipe 3 is increased, thereby improving response of the gas sensor 1. Further, since the inner bottom hole 36 do not overlap the outer bottom holes 26 as shown in FIG. 20B, condensed water is restricted from entering the element cover 2 through the outer and inner bottom holes 26, 36.

(Eighth Embodiment)

Figure 22A:
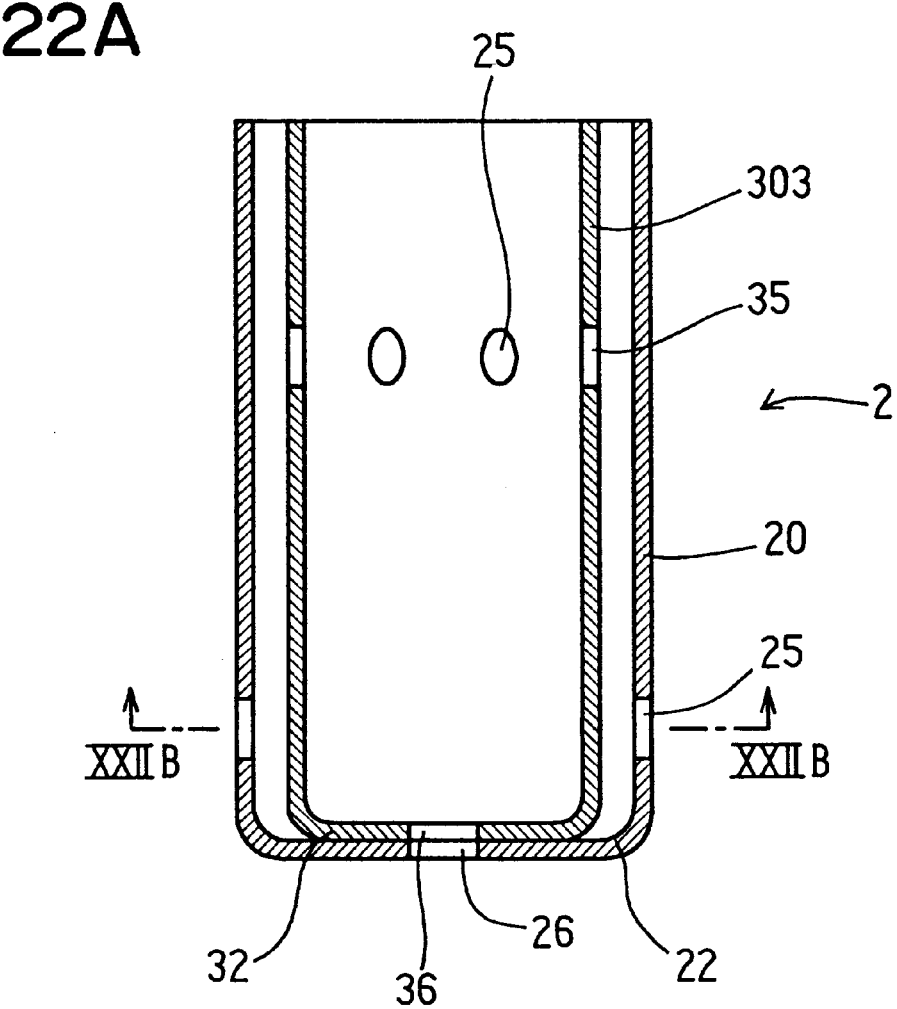
FIG. 22A is a schematic sectional view showing an element cover of a gas sensor according to an eighth preferred embodiment of the present invention.

A eighth preferred embodiment of the present invention will be described with reference to FIGS. 22A and 22B. In the eighth embodiment, the element cover 2 in the sixth embodiment is modified.

Figure 22B:
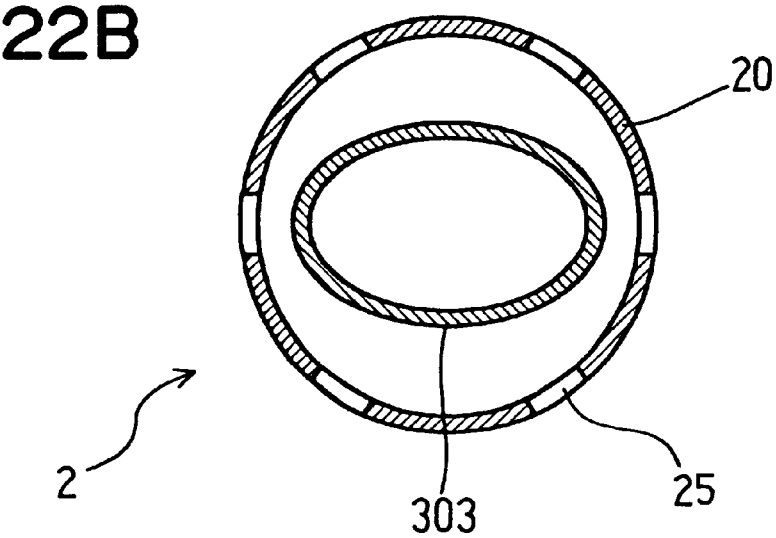
FIG. 22B is a sectional view taken along line XXIIB—XXIIB in FIG. 22A.
Figure 23:
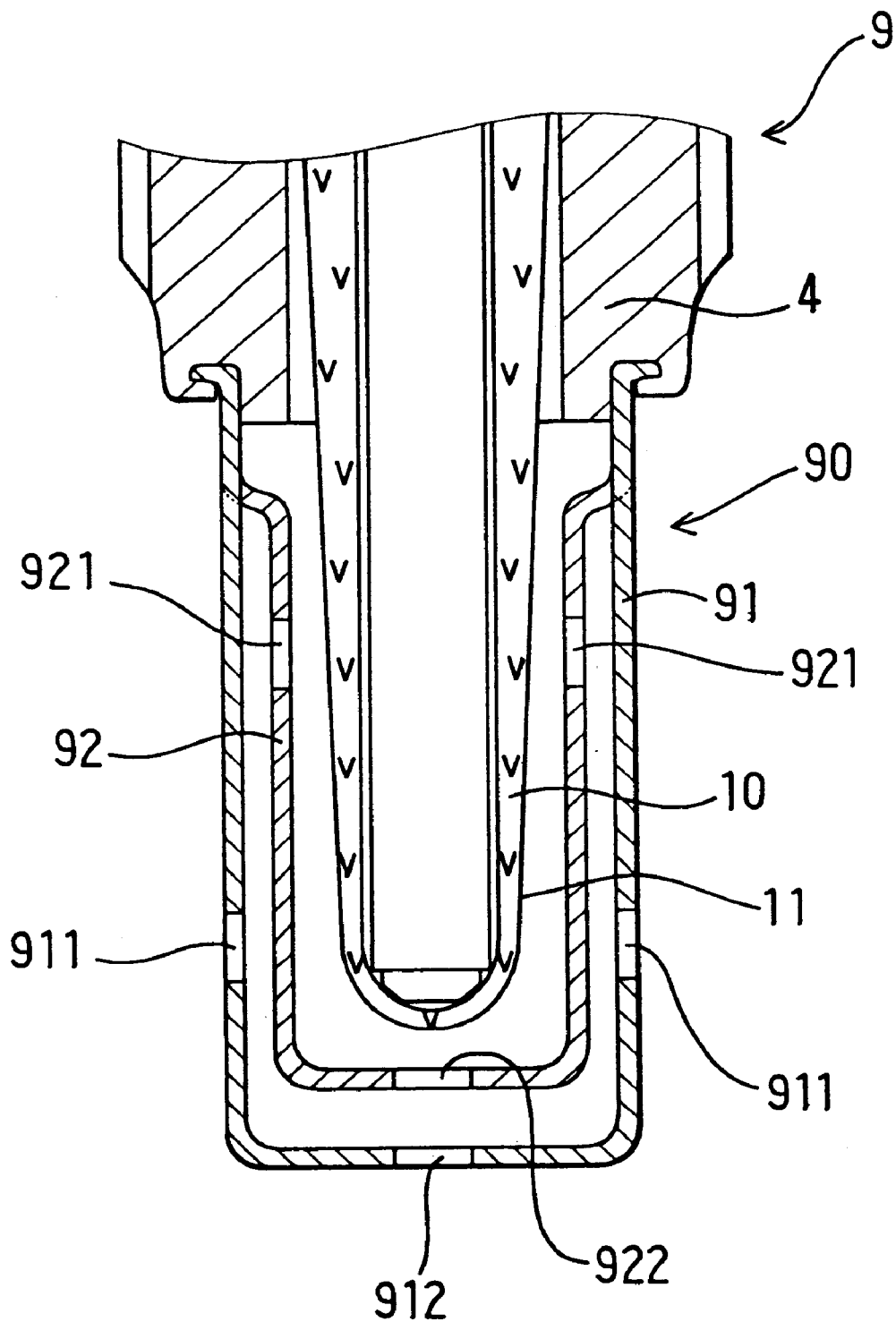
FIG. 23 is a schematic sectional view showing a gas sensing element and an element cover of a conventional gas sensor.

In the eighth embodiment, as shown in FIG. 22B, an inner pipe 303 of the element cover 2 has an oval cross-section. Therefore, a content volume of the inner pipe 303 is decreased, thereby increasing response speed of the gas sensor 1. As a result, the gas sensor 1 has faster and constant response while sufficiently preventing condensed water from entering the inside of the gas sensor 1. The element cover 2 may have a rectangular cross-section.

Although the present invention has been fully described in connection with the preferred embodiments thereof with reference to the accompanying drawings, it is to be noted that various changes and modifications will become apparent to those skilled in the art.

Such changes and modifications are to be understood as being within the scope of the present invention as defined by the appended claims.

What is claimed is:

1. A gas sensor for detecting characteristics of sample gas, said gas sensor comprising:

a housing;

a gas sensing element held by said housing and having a gas contact portion to contact the sample gas; and an element cover connected to said housing and covering said gas contact portion, said element cover having a double pipe structure formed by layering an inner pipe and an outer pipe, each of said inner pipe and said outer pipe being formed into a cylindrical shape with a bottom, wherein:

said inner pipe has a side portion including a first side portion having a side hole through which the sample gas flows and a second side portion which prevents the sample gas from flowing therethrough, and a bottom portion having a bottom hole through which the sample gas flows;

said outer pipe has a side portion having a side hole through which the sample gas flows, and a bottom portion having a bottom hole through which the sample gas flows;

said second side portion of said inner pipe is exposed through said side hole of said outer pipe; and a spacing of 0.2–1.0 mm is formed between said bottom portion of said inner pipe and said bottom portion of said outer pipe.

2. The gas sensor according to claim 1, wherein said side hole of said inner pipe is disposed more adjacent to said bottom portion of said inner pipe and said bottom portion of said outer pipe than said side hole of said outer pipe.

3. The gas sensor according to claim 1, wherein said side hole of said outer pipe is disposed more adjacent to said bottom portion of said inner pipe and said bottom portion of said outer pipe than said side hole of said inner pipe.

4. The gas sensor according to claim 1, wherein:

said bottom portion of said inner pipe has a first bottom portion including said bottom hole of said inner pipe and a second bottom portion which prevents the sample gas from flowing therethrough; and said second bottom portion of said inner pipe is exposed through said bottom hole of said outer pipe.

5. The gas sensor according to claim 1, wherein a diameter of each of said bottom hole of said outer pipe and said bottom hole of said inner pipe is 0.5–5 mm.

6. A gas sensor for detecting characteristics of sample gas, said gas sensor comprising:

a housing;

a gas sensing element held by said housing and having a gas contact portion to contact the sample gas; and an element cover connected to said housing and covering said gas contact portion, said element cover having a double pipe structure formed by laminating an inner pipe and an outer pipe, each of said inner pipe and said outer pipe being formed into a cylindrical shape with a bottom, wherein:

said inner pipe has a side portion including a first side portion having a side hole through which the sample gas flows and a second side portion which prevents the sample gas from flowing therethrough, and a bottom portion having a bottom hole through which the sample gas flows;

said outer pipe has a side portion having a side hole through which the sample gas flows, and a bottom portion having a bottom hole through which the sample gas flows;

said second side portion of said inner pipe is exposed through said side hole of said outer pipe; and the sample gas introduced into said element cover through said side hole of said outer pipe is substantially prevented from being directly discharged from said bottom hole of said outer pipe without passing through said side hole of said inner pipe.

7. The gas sensor according to claim 6, wherein said side hole of said outer pipe is disposed more adjacent to said bottom portion of said inner pipe and said bottom portion of said outer pipe than said side hole of said inner pipe.

8. The gas sensor according to claim 7, wherein:

said gas contact portion includes a sensor portion for detecting the characteristics of the sample gas; and an end portion of said sensor portion most adjacent to said bottom portion of said inner pipe is disposed more adjacent to said bottom portion of said inner pipe than an end portion of said side hole of said inner pipe most adjacent to said bottom portion of said inner pipe.

9. The gas sensor according to claim 6, wherein:

said bottom portion of said inner pipe has a first bottom portion including said bottom hole of said inner pipe and a second bottom portion which prevents the sample gas from flowing therethrough; and said second bottom portion of said inner pipe is exposed through said bottom hole of said outer pipe.

10. The gas sensor according to claim 6, wherein:

said gas sensing element is formed into a plate; and said inner pipe has any one of an oval cross-section and a rectangular cross-section.

11. The gas sensor according to claim 6, wherein:

said gas sensing element is formed into a plate;

said side hole of said inner pipe includes three and more hole portions each of which is formed into a same shape;

said hole portions are arranged in a single row extending perpendicularly to an axis of said gas sensing element.

12. The gas sensor according to claim 6, wherein a diameter of each of said bottom hole of said outer pipe and said bottom hole of said inner pipe is 0.5–5 mm.

13. The gas sensor according to claim 1, further comprising:

a protruding portion protruding from said bottom portion of said inner pipe along a circumference of said bottom hole of said inner pipe, wherein another spacing of 0.2–1.0 mm is formed between said protruding portion and said bottom portion of said outer pipe.

14. A method of guiding sample gas in a gas sensor having a gas sensing element and an element cover for covering said gas sensing element, said element cover having a double-pipe structure formed by layering an outer pipe and an inner pipe, the method comprising steps of:

introducing the sample gas into a space formed between said outer pipe and said inner pipe through a side hole of said outer pipe;

making the sample gas collide with a side portion of said inner pipe;

introducing the sample gas into said inner pipe through a side hole of said inner pipe thereby to make the sample gas contact said gas sensing element; and discharging the sample gas from a bottom hole of said inner pipe and a bottom hole of said outer pipe, wherein the sample gas is restricted from being discharged from said bottom hole of said outer pipe without flowing through said side hole of said inner pipe.

15. The method of guiding the sample gas according to claim 14, wherein a flow direction of the sample gas from said side hole of said outer pipe to said side hole of said inner pipe is substantially the same as a flow direction of the sample gas from said side hole of said inner pipe to said bottom hole of said inner pipe.

16. The gas sensor according to claim 1, wherein:

said gas sensing element is formed into a plate; and said side hole of said outer pipe is disposed more adjacent to said bottom portion of said inner pipe and said bottom portion of said outer pipe than said side hole of said inner pipe.

* * * * *